United States Patent [19]

Bobb et al.

[11] Patent Number: 5,115,127
[45] Date of Patent: May 19, 1992

[54] OPTICAL FIBER SENSOR FOR MEASURING PHYSICAL PROPERTIES OF FLUIDS

[75] Inventors: Lloyd C. Bobb, Warminster, Pa.; Barbara J. White, Hatboro; Jon P. Davis, Willow Grove, all of Pa.; Arthur Samouris, Albuquerque, N. Mex.

[73] Assignee: The United States of America as represented by the Secretary of the Navy, Washington, D.C.

[21] Appl. No.: 585,331

[22] Filed: Sep. 17, 1990

Related U.S. Application Data

[63] Continuation-in-part of Ser. No. 460,435, Jan. 3, 1990, Pat. No. 5,047,626.

[51] Int. Cl.⁵ .......................... H01J 5/16; G01D 5/34
[52] U.S. Cl. .......................... 250/227.19; 250/231.1; 324/96
[58] Field of Search ............. 250/227.19, 231.1; 324/96; 350/96.29; 356/44, 72, 357–359

[56] References Cited

U.S. PATENT DOCUMENTS

| | | | |
|---|---|---|---|
| 4,448,526 | 5/1984 | Miyazawa | 324/96 |
| 4,494,656 | 1/1985 | Shaw et al. | 250/227.19 |
| 4,530,603 | 7/1985 | Shaw et al. | 250/227.19 |
| 4,546,247 | 10/1985 | Peyton et al. | 324/96 |
| 4,563,639 | 1/1986 | Langeac | 250/227.17 |
| 4,621,929 | 11/1986 | Phillips | 356/44 |
| 4,627,728 | 12/1986 | Willson | 250/227.19 |
| 4,929,050 | 5/1990 | Wilson | 250/227.19 |
| 5,047,626 | 9/1991 | Bobb et al. | 250/227.19 |

Primary Examiner—David C. Nelms
Assistant Examiner—S. Allen
Attorney, Agent, or Firm—James V. Tura; James B. Bechtel; Susan E. Verona

[57] ABSTRACT

A physical property of a fluid or of any optical fiber is measured using an optical fiber interferometer. A conductive material is disposed upon the surface of a region of a light tranmitting optical fiber and the region having the conductive material is disposed in the fluid. Light energy is applied to one end of the fiber and transmitted light is received at the other end of the fiber. Electrical energy is applied to the conductive material disposed upon the surface of the fiber to heat the region of the fiber and cause a change in the optical path length of the light transmitted through the fiber. The physical property of the fluid or optical fiber is determined in accordance with the change in the optical path length or phase of the received light caused by applying the electrical energy to the conductive material. Thermal conductivity is measured using a series of short energy pulses and determining the average phase change. The flow rate of a fluid is measured by measuring the phase change and applied electrical energy upon heating the fiber to an equilibrium temperature. The conductive material is gold and it encircles the fiber. The gold may be disposed on the jacket of the fiber or the jacket may be removed before disposing the gold.

2 Claims, 5 Drawing Sheets

OPTICAL FIBER SENSOR FOR MEASURING PHYSICAL PROPERTIES OF FLUIDS

STATEMENT OF GOVERNMENT INTEREST

The invention described herein may be manufactured and used by or for the Government of the United States of America for governmental purposes without the payment of any royalties thereon or therefor.

CONTINUING APPLICATION

This application is a continuation-in-part of copending application Ser. No. 07/460,435, filed Jan. 3, 1990.

BACKGROUND OF THE INVENTION

This invention relates to a device and method for measuring the physical properties of fluids, including liquids and gases, and in particular to a device and method for measuring physical properties of fluids using the interference of light waves.

The thermal conductivities of liquids are often measured because the thermal conductivities of liquids are required for various heat transfer analyses. These conductivities are commonly obtained with a transient hot-wire apparatus. In this technique a thin platinum wire, serving as both a heating element and a thermometer, is heated resistively with a current pulse of about one second duration. The thermal conductivity of the surrounding medium is determined from the temperature change of the wire as a function of time. In this type of analysis an approximate solution of the heat conduction equation is used, where the slope of the change in temperature versus the natural log of time curve is inversely proportional to the thermal conductivity of the medium. In applying this method, a number of corrections are necessary due to the finite diameter and finite thermal conductivity of the platinum wire. Additionally, a correction for the temperature dependence of the fluid properties is necessary. With these corrections incorporated into the analysis, the technique allows for thermal conductivity determinations with an accuracy of 0.2%.

Similarly, gas flow rates can be measured with a hot-wire anemometer, which employs a fine wire mounted transversely to the gas flow. The wire is heated by an electrical current and the temperature rise, which depends inversely on the flow rate, is determined by the resistance change of the wire.

Because electrical sensing devices can be a source of explosion hazard when monitoring flammable liquids, fiber optic systems for measuring properties such as temperature, thermal conductivity, and flow rate are preferred. Such fiber optic systems for measuring temperature are well-known in the art. One such system is disclosed in Langeac U.S. Pat. No. 4,563,639, in which a probe is formed by winding an optical fiber in a generally solenoid shape. U.S. Pat. No. 4,621,929, issued to Phillips and entitled "Fibre Optic Thermal Anemometer," teaches a device for measuring the heat transfer coefficient of a sample by implanting in the sample an element with temperature-sensitive optical properties. The element is heated or cooled and the temperature difference between the element and the unheated sample and the rate of heating or cooling indicate the heat transfer coefficient of the sample. An optical fiber is connected to the element for transmitting radiation to and from the element. The fiber serves as a conduit rather than as the sensing element itself.

Optical fibers have been used previously as flow or velocity sensors. Pitt et al. have discussed several types of optical fiber flowmeters ranging from simple pulsed interruption methods with turbine impeller blades to vortex shedding and correlation techniques ("Optical Fiber Flowmeters", Proc. 2nd International Conference on Optical Fiber Sensors, Stuttgart, pp. 23-28, September 1984). Wide and Dandridge have described a fiber optic mass flowmeter for liquids which utilizes the Coriolis effect ("Fibre-Optic Coriolis Mass Flowmeter for Liquids," Electr. Lett. 24, 783, 1988). Fiber optic techniques have also been utilized in laser-Doppler anemometry. The Phillips patent discloses the use of his fiber optic device to measure flow. The temperature-sensitive element is heated with near infrared radiation which passes through the same optical fiber that optically communicates with the temperature sensor. The change in temperature produced by the infrared radiation is inversely dependent upon the flow rate of the fluid past the sensor. Again, the optical fiber is used to transmit the light to or from the sensor, and not as the sensing element.

U.S. Pat. No. 4,859,059, issued to Bobb et al. and entitled "Thermal Modulation of Light Beams" discloses controlling phase in an interferometer by electrically heating a gold-coated section of an optical fiber in the interferometer.

SUMMARY OF THE INVENTION

It is a general object of the present invention to provide a method and an apparatus for measuring the physical properties of fluids, such as liquids and gases.

It is a specific object to measure physical properties of fluids using an optical fiber interferometer.

It is another specific object to provide a method and an apparatus for measuring the thermal conductivities of fluids.

It is yet another specific object to provide a method and an apparatus for measuring the flow rate of a fluid.

These and other objects are accomplished by a method and apparatus in which a physical property of a fluid, such as a liquid or a gas, is measured using a light transmitting optical fiber interferometer. A conductive material is disposed upon the surface of a region of the light-transmitting optical fiber and the region having the conductive material is disposed in the fluid. Light energy is applied to one end of the fiber and transmitted light is received at the other end of the fiber. Electrical energy is applied to the conductive material disposed upon the surface of the fiber to heat the region of the fiber and cause a change in the optical path length or phase of the light transmitted through the fiber. The physical property of the fluid or of the optical fiber itself is determined in accordance with this change, which can be detected by an interferometer as a change in interference of received light. The thermal conductivity or flow rate of a fluid can be determined using the present invention.

These and other objects, advantages, and novel features will become apparent from the following detailed description of the invention when considered in conjunction with the accompanying drawings.

DETAILED DESCRIPTION OF THE INVENTION

Figure 1:
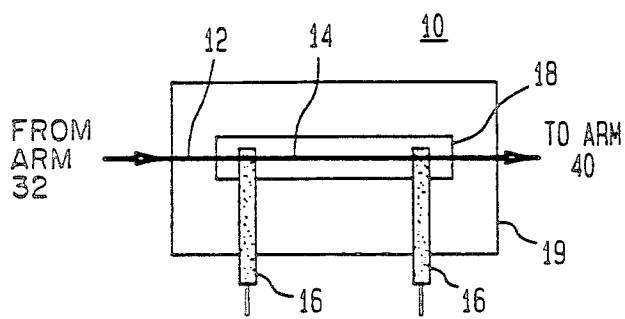
FIG. 1 shows the cell of the optical fiber sensor of the present invention for measuring the physical properties of fluids.

Referring now to the drawings wherein like characters designate like or corresponding parts throughout the several views, one sees in FIG. 1 a cell 10 for measuring the physical properties to a fluid. An optical fiber 12 is positioned within cell 10 and has disposed on the surface thereof a thin layer 14 formed of a conductive material such as gold. Gold layer 14 completely surrounds a length of fiber 12 which may range from one to two-and-one-half centimeters and may be sputtered onto the surface of the fiber to a thickness of approximately one-tenth of a micron.

Figure 2A:
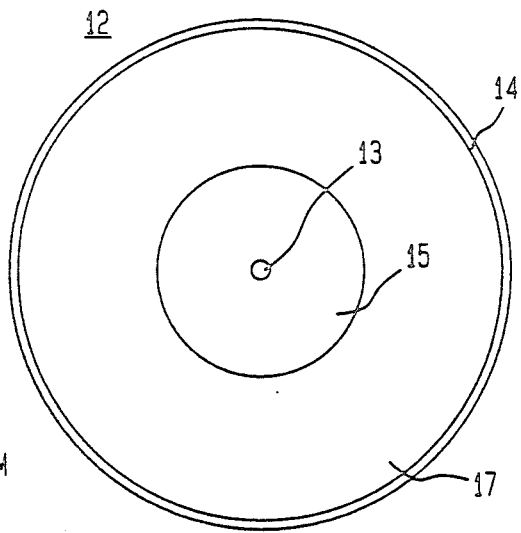
FIGS. 2a,b show cross-sectional representations of a conductor-coated region of an unjacketed optical fiber and a jacketed optical fiber, respectively, of the cell of the present invention.
Figure 2B:
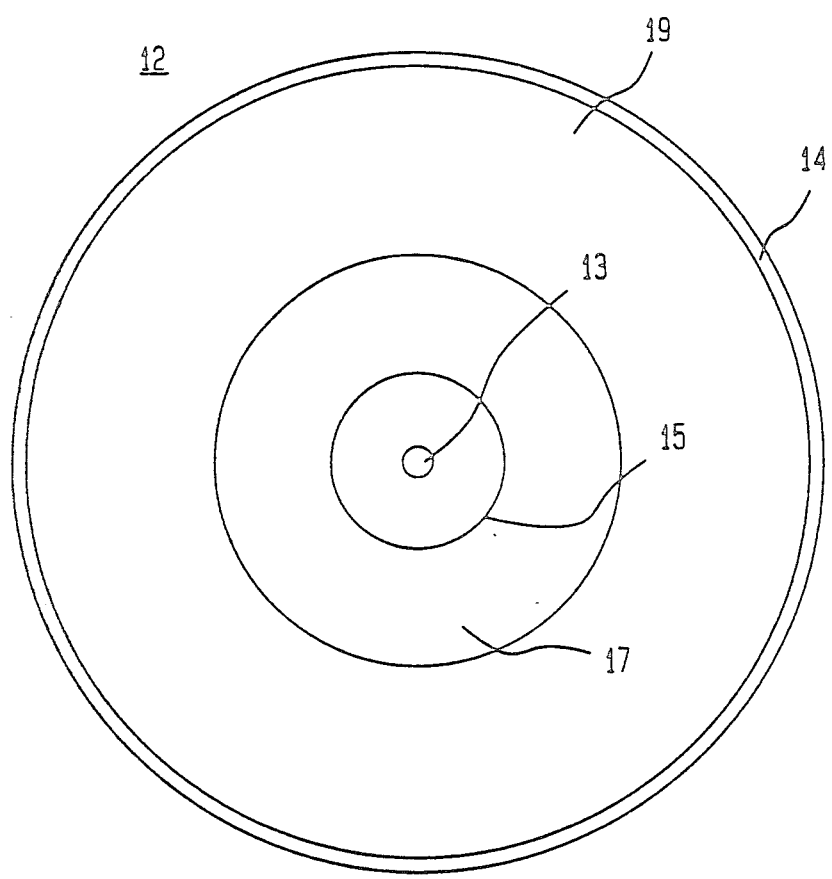

FIGS. 2a and 2b show cross-sectional views of optical fiber 12 having gold layer 14 thereon. Fiber 12 is a single mode optical fiber for transmitting light from a coherent, single frequency laser source. Such a fiber is an ITT Type T-1601 having a four micron diameter silica core 13, a forty micron outside diameter $B_2O_3$-doped silica cladding 15, an eighty five micron outside diameter silica substrate 17, and a silicone/plastic jacket 19. Jacket 19 may be removed from the length of fiber 12 on which gold layer 14 is disposed, as shown in FIG. 2a, or the gold layer may be deposited directly on jacket 19, as shown in FIG. 2b.

The section of fiber 12 having gold layer 14 is disposed in well or passageway 18 of block 21. Block 21 may be composed of insulating material to minimize temperature drift. The fluid being monitored is placed in well or passageway 18 or, if flow rate is t be measured, positioned to flow through the well or passageway to permit immersion of gold layer 14 in the fluid. Electrical energy is applied to gold layer 14 via electrodes 16, which are electrically coupled to the layer with silver paint, causing the layer to heat up resistively, thereby causing the temperature of fiber 12 to heat up as well. The change in temperature of fiber 12 is influenced by various physical properties of the fluid, including its thermal conductivity and, if it is flowing, its flow rate. Therefore, by monitoring the fiber 12 temperature change, these and other properties can be determined.

The temperature rise of optical fiber 12 due to the applied electrical energy is determined by measuring the change in the optical path length or phase of coherent, single-frequency light transmitted through the fiber. The phase of a wave propagating in fiber 12 of length L is given by $$\phi = 2\pi n L / \lambda \qquad (1)$$

where n is the effective refractive index, which may be approximated by the refractive index of core 13 of fiber 12, and $\lambda$ is the wavelength of the light in free space. A change in fiber 12 temperature T results in a proportionate phase shift $\Delta\phi$ of the light in fiber 12 because of the temperature-induced change in the refractive index n of core 13 of fiber 12, the change in the length L of fiber 12 due to thermal expansion, and the photoelastic effect. This phase shift $\Delta\phi$ can be measured by observing the interference of the light through fiber 12 with light from the same source which is unaffected by the temperature change. The interference pattern which occurs therefore changes with the changing temperature. A change in the interference patter is detected as a change in the intensity of the combined light.

Figure 3:
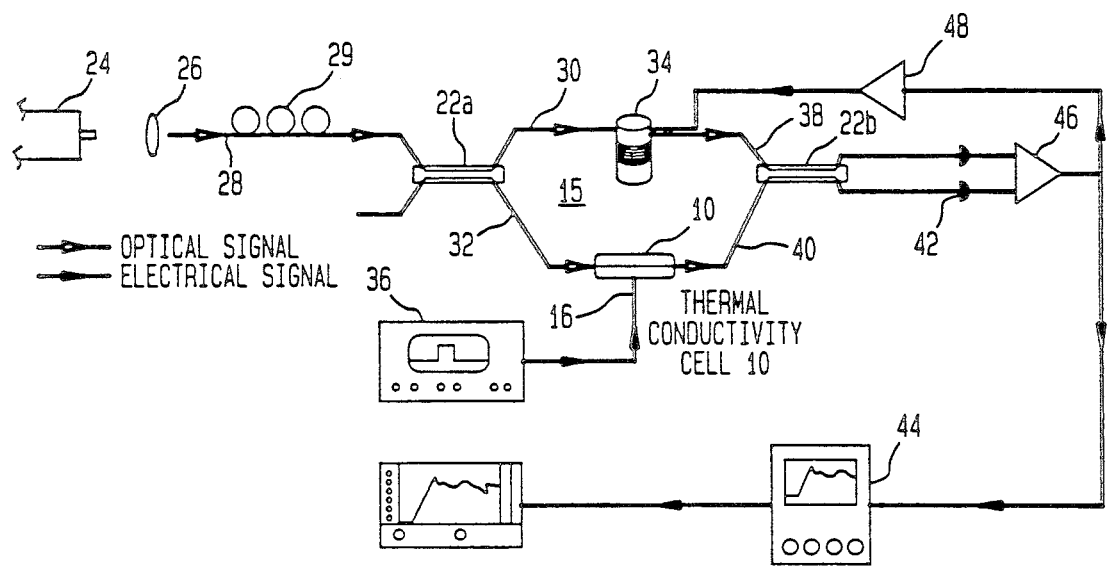
FIG. 3 shows the experimental apparatus used to test the sensor of the present invention for measuring thermal conductivity including a Mach-Zehnder interferometer.

In FIG. 3, the means and apparatus are shown for measuring the phase shift and changing interference pattern using a Mach-Zehnder interferometer system 20, wherein cell 10 forms one arm of a Mach-Zehnder interferometer 15. Any optical fiber interferometer may be used. Interferometer system 20 also includes single-mode couplers 22a,b which may be 3dB 2×2 Amphenol couplers. Light from a coherent, single-frequency source, such as a single-frequency helium-neon laser 24 is applied by way of lens 26 to the end of input fiber 28 having polarization controller 29. The light is split evenly between fiber sections 30, 32 of interferometer 15 at first coupler 22a. Fiber section 32 of interferometer 15 is coupled to cell 10. Fiber section 30 of interferometer 15 may include a PZT stretcher 34 to maintain the interferometer at quadrature. The light from fiber section 40, which is affected by the measurement occurring in cell 10, is combined with light from fiber section 38 at coupler 22b and exits through coupler 22b to be collected by photodiodes 42 for comparison by differential amplifier 46. The electrical signals from differential amplifier 46, which are proportional to the change in the intensity of the combined light, are recorded and stored by signal analyzer 44. Signal analyzer 44 may, for example, be an HP 3651A Signal Analyzer. Feedback from differential amplifier 46 may also be applied to PZT fiber stretcher 34 by way of locking amplifier 48, if quadrature is to be maintained. Gold-coated fiber 12 in cell 10 is resistively heated by voltage or current pulses from pulse generator 36 via electrodes 16. It can be seen, then, that the single section of fiber 12 having gold layer 14 disposed thereupon serves as both the heating element and the thermometer of interferometer system 20.

The use of the method and apparatus for measuring the thermal conductivity of liquids is demonstrated by the following description of an experiment, wherein cell 10 becomes a cell for measuring thermal conductivity. Gold-coated fiber 12 is immersed in the liquid in well 18 of block 21. Approximately 1.4 cubic centimeters of the fluid are sufficient for this measurement. The electrical energy is applied to gold layer 14 and the temperature rise of optical fiber 12 due to the applied electrical energy is determined by monitoring the interference pattern generated when light is launched into interferometer 15, as described above. Since this temperature is influenced by the thermal conductivity of the liquid, the thermal conductivity of the liquid may be determined in accordance with the measured light or interference pattern.

This thermal conductivity measurement requires a temperature rise of only tenths of a degree of the optical fiber 12 in thermal conductivity cell 10. Gold-coated fiber 12 is therefore resistively heated repeatedly with one millisecond voltage or current pulses with a one percent duty cycle from pulse generator 36. Each pulse from pulse generator 36 produces a time-dependent signal which is proportional to the optical phase change in fiber section 32 containing thermal conductivity cell 10 because temperature changes of fiber 12 within gold layer 14 are observed as a shifting of the interference pattern. Because of the small temperature rise, small shifts are monitored and quadrature is therefore maintained with PZT stretcher 34 and locking amplifier 48. In the experiment, the time-averaged signal produced by one hundred such pulses was recorded. The corrections associated with the temperature dependence of the fluid properties are unnecessary, since the temperature rise is very small. In addition, heat conduction is determined numerically for the regions inside and outside of fiber 12 so that no corrections associated with the approximate solution are required. Another advantage associated with the short-time measurement of the thermal conductivity cell 10 is the minimization of possible convective losses which would unnecessarily complicate the thermal conductivity determination. The time delay associated with the onset of convection is much greater than the pulse times used.

The temperature sensitivity of gold-coated fiber 12 may be determined both theoretically and experimentally. In the experimental determination, microdegree temperature changes are observed. Using the theoretical determination concerning the phase of light propagating through a fiber, as discussed above, and the relationship between temperature and phase, the temperature sensitivity of the gold-coated section of fiber 12 may be expressed as $$\Delta\phi/L\Delta T = (2\pi/\lambda)[(\epsilon n/\epsilon T)_p - n\epsilon_z/\Delta T - (n^3/2\Delta T)\{-P_{11} + P_{12})(\epsilon_r + P_{12})\epsilon_r - P_{12}\epsilon_z)\} \quad (2)$$

where $\rho$ is the core density, $\epsilon_Z$ and $\epsilon_r$ are the axial and radial strains, and $P_{11}$ and $P_{12}$ are the Pockels coefficients. Fiber 12 is considered to consist of four concentric layers: core 13, cladding 15, substrate 17, and the one-tenth micron gold layer 14. The strains resulting from the temperature change $\Delta T$ are calculated using the method of Schuetz et al. ("Dynamic Thermal Response of Single-Mode Optical Fiber for Interferometric Sensors," Appl. Opt. 22, 478 (1983)). The sensitivity for the unjacketed fiber thus determined is $\Delta\phi/L\Delta T = 16.3$ fringes/m-° C. where the first term in equation (2) provides the major contribution.

The temperature sensitivity of gold-coated fiber 12 may also be determined experimentally by monitoring the resistance change of the gold film 14 when heated by a steady current. The temperature change is then calculated as $$\Delta T = \Delta R \, R\gamma_t \quad (3)$$

where $\Delta R$ is the resistance change corresponding to a temperature change $\Delta T$. R is the room temperature resistance, and $\gamma_t$ is the temperature coefficient of resistivity. A value for $\gamma_t$ is determined experimentally by placing gold layer 14 of fiber 12 in a furnace (not shown) and monitoring the resistance as the temperature is increased. These experimental results are then used to obtain the experimental temperature sensitivity of $$\Delta\phi/L\Delta T = 15.9 \, fringes/m\text{-}° C. \quad (4)$$

The experimental value is in reasonable agreement with the theoretical value, and is the value used in the thermal conductivity analyses. The greatest experimental uncertainty is the accurate determination of the coated length L of fiber 12. In practice it is most convenient to calibrate the thermal conductivity sensor with a fluid of known thermal conductivity; in the measurements discussed below, pure ethylene glycol is taken as a standard with a thermal conductivity of 0.255 W/m-° C.

Figure 4:
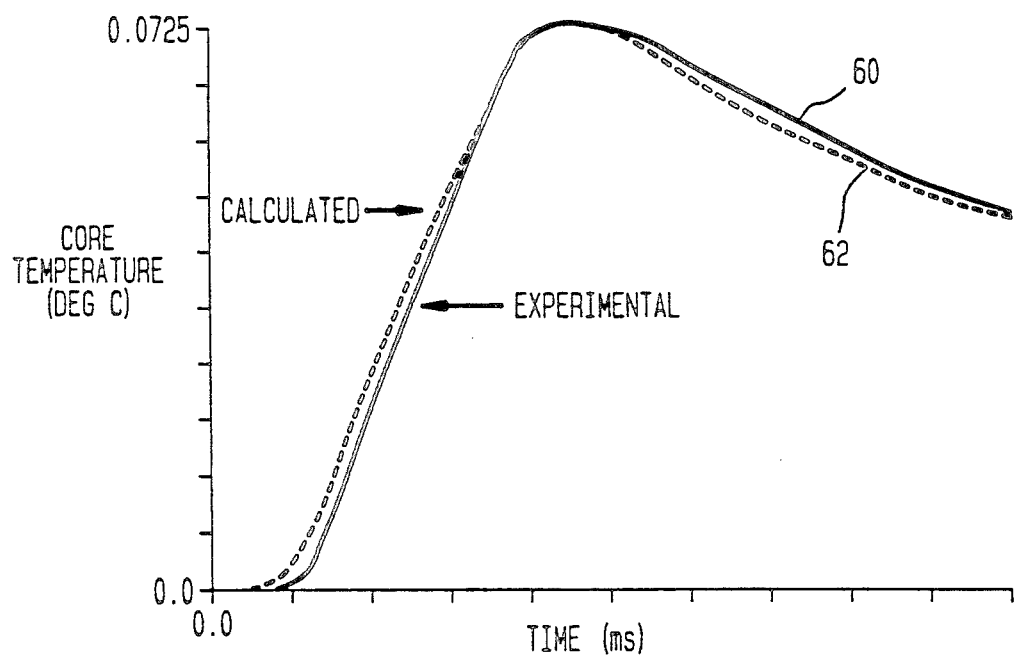
FIG. 4 shows the core temperature of the fiber of FIG. 1 as a function of time when a one millisecond square pulse is applied to a conducting region disposed on the surface of the fiber of FIG. 1 while measuring the thermal conductivity of a liquid.

The experimental data are recorded as optical phase changes which are related to $\Delta T$ through equation (4). A typical plot of T versus time t for water is shown as curves 60, 62 in FIG. 4, wherein curve 60 represents the experimentally obtained response and curve 62 represents the calculated response. Curve 60 represents the average response to one hundred consecutive one-millisecond pulses. If gold-coated fiber 12 is immersed in a fluid medium of lower thermal conductivity, the risetime of curve 60 is shorter, the peak is higher and the decay time is longer. The peak value of the temperature rise provides the most convenient measure of the thermal conductivity; thus, the data presented below are obtained through measurement of the peak heights.

An interpretation of the experimental data is provided through a numerical solution of the heat conduction equation.

$$\partial\Delta T/\partial t = K\nabla^2\Delta T + P/\rho C_p A \quad (5)$$

where $K = K/\rho C_p$ is the diffusivity, K is the thermal conductivity, $C_p$ is the specific heat at constant pressure, A is the cross-sectional area of the heated region, P is the power applied to the fiber per unit length, and $\rho$ is the density. An infinite length and circular symmetry are assumed, and equation (5) is solved in two regions: the silica fiber and the surrounding liquid medium whose thermal conductivity is to be determined. The material properties $\rho$ and $C_p$ for both the fiber 12 and the medium must be separately measured, obtained from the literature, or determined by the present method. Equation (5) is replaced by a finite difference equation which is solved using boundary conditions $\partial\Delta T/\partial r = 0$ at $r = 0$ and $\Delta T = 0$ at $r = R$ and initial conditions $\Delta T = 0$. The outer radius R of the medium is taken to be much greater than the thermal diffusion length for the time period employed in the calculation. Gold coating 14 is assumed to have a negligible thickness and the power dissipation in gold coating 14 is assumed to occur in the boundary region between the fiber 12 and the fluid medium. The finite-difference approximations yield a set of coupled first-order ordinary differential equations in the time variable. These differential equations are then solved by the standard Bulirsch-Stoer Method.

The entire $\Delta T$ versus time curve is a sensitive function of the material parameters. For example, a five micron change in the fiber outer-diameter used in the calculations produces an easily discernible change in the calculated curve 62. Thus the method of the present invention may be used to determine the parameters of fiber 12 as well as the properties of the liquid. The calculations for curve 62 are performed using a handbook value of $K_{silica} = 1.34$ W/m-° C., a value for generic silica. A ten percent reduction of $K_{silica}$ to 1.21 W/m-° C. makes the calculated and experimental curves almost indistinguishable at the resolution shown in FIG. 4.

Experimental results are presented for aqueous ethylene glycol solutions. Handbook values of the density and specific heat and literature values of the thermal conductivity are shown in Table I.

TABLE I

| Solution Properties at 20° C. | | | |
|---|---|---|---|
| Concentration (Weight % eth gly) | Density (kg/m³ · 10⁻³) | Specific Heat (J/kg·°C. · 10⁻³) | Thermal Conductivity (W/m-°C.) |
| 0 | 1.000 | 4.186 | 0.599 |
| 20 | 1.0241 | 3.906 | 0.508 |
| 40 | 1.0514 | 3.516 | 0.423 |
| 60 | 1.0765 | 3.119 | 0.356 |
| 80 | 1.0960 | 2.729 | 0.298 |
| 100 | 1.1130 | 2.344 | 0.255 |

Figure 5:
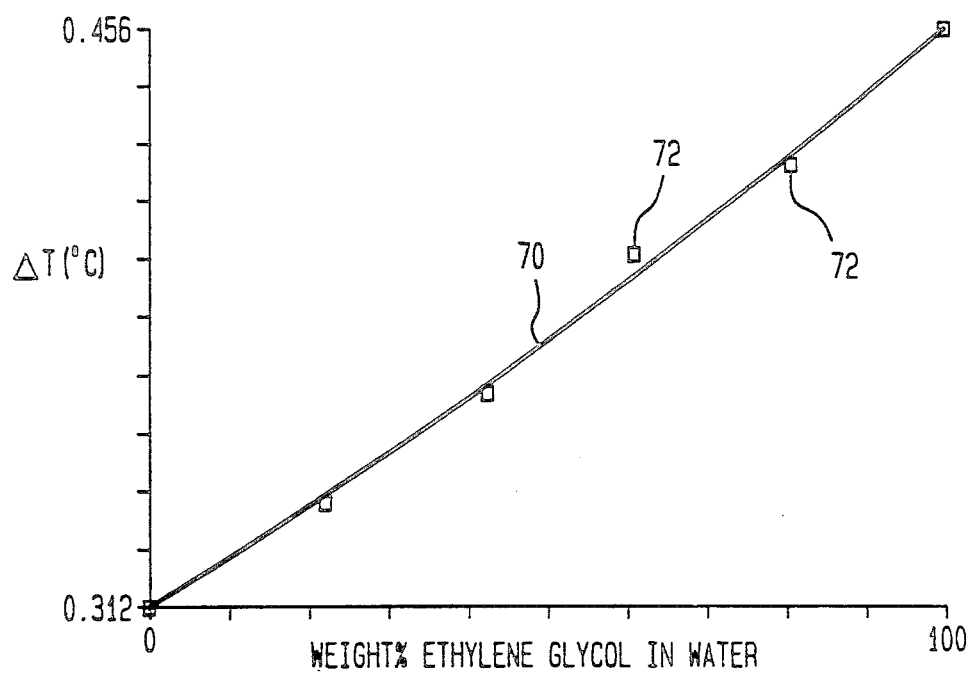
FIG. 5 shows a graphical representation of the variation of peak core temperature of the fiber of FIG. 1 as a function of the concentration of ethylene glycol in water while measuring the thermal conductivity thereof.

The date given in Table I are used to calculate the maximum core temperatures for an applied power of 5.90 W/m for the six solutions. The maximum core temperatures are also measured for solutions of 0, 20, 40, 60, 80, and 100% ethylene glycol by volume. The experimental and calculated results are shown as points 72 and curve 70, respectively, in FIG. 5. Similar agreement is obtained for other power levels. Conversely, thermal conductivity cell 10 of the present invention may be used to measure the concentration as well as the diffusivity and other physical properties of a liquid.

In the comparison between theory and experiment, the heat capacity of gold layer 14 itself has been ignored. This effect is most important at early times and produces a temperature reduction of less than two percent for times greater than one tenth of a millisecond. The second effect ignored is the temperature non-uniformity of fiber 12. This effect is also most important at early times and appears as a temperature increase of less than one percent of peak value for the first couple tenths of a millisecond.

For well-known fiber material parameters, the present technique can determine $(\rho C_p)$ as well as K for the medium. Equation (5) is invariant on multiplication of $\Delta T$ and $(P/\rho C_p A)$ by the same factor. Therefore, normalized plots of $\Delta T$ versus time will depend only on $\kappa_{medium}$ ($\kappa_{medium} = K/\kappa C_p =$ diffusivity). $\kappa_{medium}$ can thus be obtained from the normalized plots. Knowing $\kappa_{medium}$, P, and A, the peak height gives $(\rho C_p)$ which can then by used to obtain $K_{medium}$.

A gold-coated jacketed fiber 12 or a gold-coated unjacketed fiber 12 may be provided for conductivity cell 10 of the present invention. Thermal conductivity cell 10 formed with a gold-coated jacketed fiber 12 is more than twice as sensitive as gold-coated unjacketed fiber 12.

Some of the advantages of the present invention as a thermal conductivity sensor should now be readily apparent. A short-time heating technique is used wherein solution temperature changes of tenths of a degree are produced. The classical hot-wire approach uses heating times of longer duration and produces larger temperature changes in the fluid being measured. For this reason many corrections are required for accurate measurements. The short-time approach eliminates these corrections but requires a more complex numerical solution of heat conduction equation (5). Additionally, greater sensitivity is achieved using the present invention.

Figure 6:
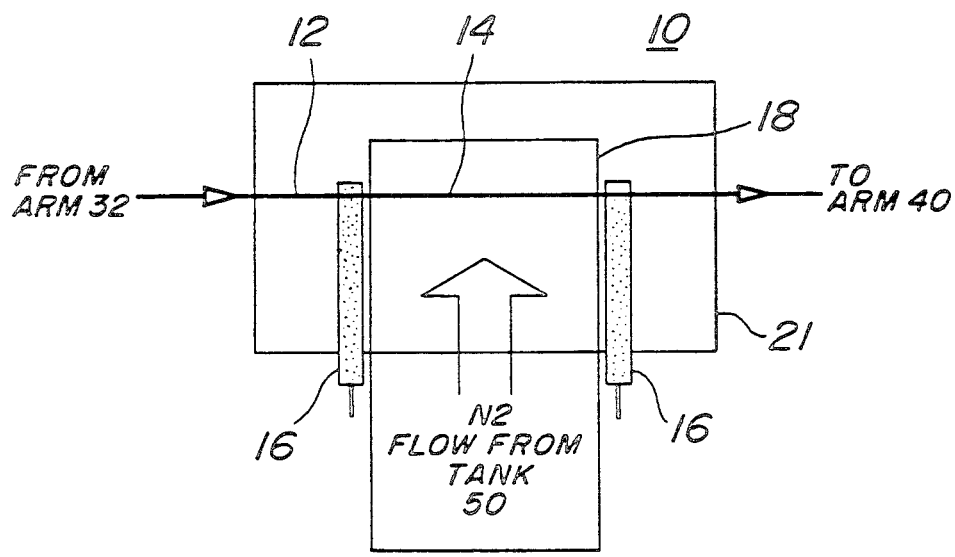
FIG. 6 shows the cell of the optical fiber sensor of the present invention adapted to measure the flow rate of a fluid.
Figure 7:
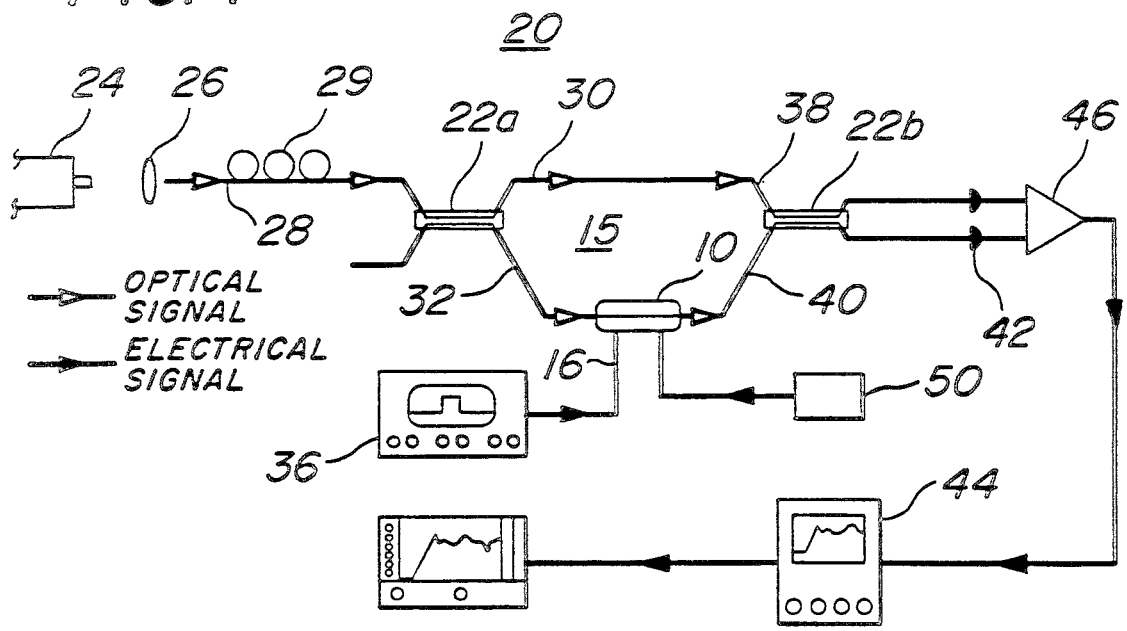
FIG. 7 shows the experimental apparatus used to test the sensor of the present invention for measuring the flow rate of a fluid.

The device and method of the present invention may also be used to measure the flow rate of a fluid. As shown in FIGS. 6 and 7, fiber 12 with gold layer 14 is disposed in the flowing fluid in cell 10, preferably transversely to the direction of flow. Cell 10 for measuring flow rate is shown, wherein well or passageway 18 is connected to receive flowing fluid from tank 50. Electric energy of a predetermined value from pulse generator 36 is applied to conductive coating 14 for a length of time long enough to resistively heat fiber 12 to an equilibrium temperature. The power required to maintain equilibrium is noted. Since the optical path length of the light traveling through the optical fiber changes proportionately with the temperature thereof, the light from source 24 traveling through fiber 12 is shifted in phase. This phase shift can be detected as a change in the interference pattern between the two light waves. A change in the interference pattern is detected as a change in the intensity of the combined light from fiber sections 38 and 40. This change in light intensity is detected by photodiodes 42, which convert the light intensity into electrical signals which are proportional thereto. These electrical signals are transmitted to signal analyzer 44 which then displays them graphically as sine waves. These sine waves are proportional to the number of periods (or fringes) out-of-phase which the light through fiber 12 has shifted relative to its initial phase. Knowing the relationship of the temperature of fiber 12 to the optical path length of the light through the fiber and hence to the phase shift, one can determine the temperature change of the fiber from the starting time of the applied electrical energy until the time when equilibrium was reached by counting the number of fringes generated during that same time. Because whole fringes are counted as opposed to fractions of one fringe, the device is not maintained in quadrature, and therefore PZT stretcher 34 and locking amplifier 48 are eliminated, as shown in FIG. 7. In this case fiber section 30 is optically connected to fiber section 38. Using equations relating temperature change from start to equilibrium to the amount of power being supplied to coating 14 at equilibrium, one can determine the flow rate of the fluid in which fiber 12 is immersed.

The use of the method and apparatus for measuring the flow of a fluid is demonstrated by the following description of an experiment. Gold coating 14 is 0.1 micron thick and covers a 1 cm length of unjacketed silica fiber 12. An ITT Type 1601 single-mode optical fiber having the above-described dimensions was used in this study. The coated section of fiber 12 was mounted transversely within a 1-cm diameter well or passageway 18 through which nitrogen gas from tank 50 flowed. Fiber 12 was heated resistively by applying a repetitive 5-sec square-wave voltage with a power of 0.0976 W and a 50% duty cycle from pulse generator 36. The output from interferometer 15 was recorded on an HP 3561A Dynamic Signal Analyzer 44. Light was supplied from single-frequency helium-neon laser 24. In this manner it was possible to measure the actual phase shift by counting the number of fringes produced upon application and/or removal of the square-wave voltage.

Lateral heat transfer from heated fiber 12 occurs primarily by the mechanism of forced convection, although thermal conduction occurs at short times and free and mixed convection occur at very low flow rates. Due to the low emissivity gold coating 14, lateral radiation heat transfer is negligible. In addition heat transfer occurs along the fiber 12 by conduction. A simple model which assumes uniform lateral fiber temperature and a temperature-independent convection coefficient is useful in interpreting the data. When fiber 12 is heated with a square-wave voltage pulse with initial power $P_o$, the fiber temperature will increase, and the final temperature of the fiber $T_f$ (relative to the ambient temperature) as a function of the distance x from the center of the fiber can be obtained from the following differential equation:

$$k'd^2T_f/dx^2 - 2\pi ahT_f - P_f/L = 0 \qquad (6)$$

where the first term accounts for the longitudinal heat flow by conduction, the second term for lateral convective heat flow, and the third term for the input power. In equation (6), a and L are the outer radius and length of the coated fiber, h is the convection coefficient, $k' = k(silica)A(silica) + k(gold)A(gold)$, k is the thermal conductivity, A is the cross-sectional area, and $P_f$ is the final power. The solution to equation (6) satisfying the boundary conditions $T_f = 0$ for $x = \pm L/2$ is $$T_f(x) = (P_f/2\pi ahL)\{1 - cosh[(2\pi ah/K')^{\frac{1}{2}}X]/cosh[(\pi ah/4K')^{\frac{1}{2}}L]\} \qquad (7)$$

The average temperature is then found to be $$T_a = (1/L)\int T_f dx = \{(P_f/2\pi ahL)\}\{1 - (2/L)(K'/2\pi ah)^{\frac{1}{2}} tanh[(\pi ah/2k')^{\frac{1}{2}}L]\} \qquad (8)$$

In equations (6) to (8) the final power may be approximated as $$P_f = P_o/(1 + \alpha T_a) \qquad (9)$$

where α is the temperature coefficient of resistance for the gold film. If equation (9) is substituted into equation (8), a transcendental equation is obtained for the average fiber temperature $T_a$ as a function of the convection coefficient h.

The average fiber temperature $T_a$ may also be related to the phase change $\Delta\phi$ of light propagating in the gold-coated length of the fiber. A change in fiber temperature $T_a$ results in a phase shift $\Delta\phi$ of the light in the fiber as discussed above in relation to the theoretical determination of sensitivity and equations (1) and (2). The phase change for this experimental configuration was calculated to be $\Delta\phi = 16.3 T_aL$ fringes, as it was for the thermal conductivity experiment.

The phase change in gold-coated fiber 12 was also determined experimentally in the same manner as it was for the thermal conductivity experiment. These experimental results were then used to obtain a phase change of $$\Delta\phi = 15.9 T_aL \text{ fringes} \qquad (10)$$

In general the number of fringes produced as a function of time could by represented by an equation of the form $\phi(t) = \Delta\phi[1-\exp(-t/\tau)]$, and an exponential fit was used to determine $\Delta\phi$. In the series of experiments using a 5-S, 0.9 V pulse and a nitrogen flow rate of 0.38 m/s, the total number of fringes was determined to be $\Delta\phi = 14.3$ both upon application and removal of the voltage pulse. Using equation (10) with L = 0.01 m the corresponding average fiber temperature change is calculated to be $T_a = 89.9°$ C.

Figure 8:
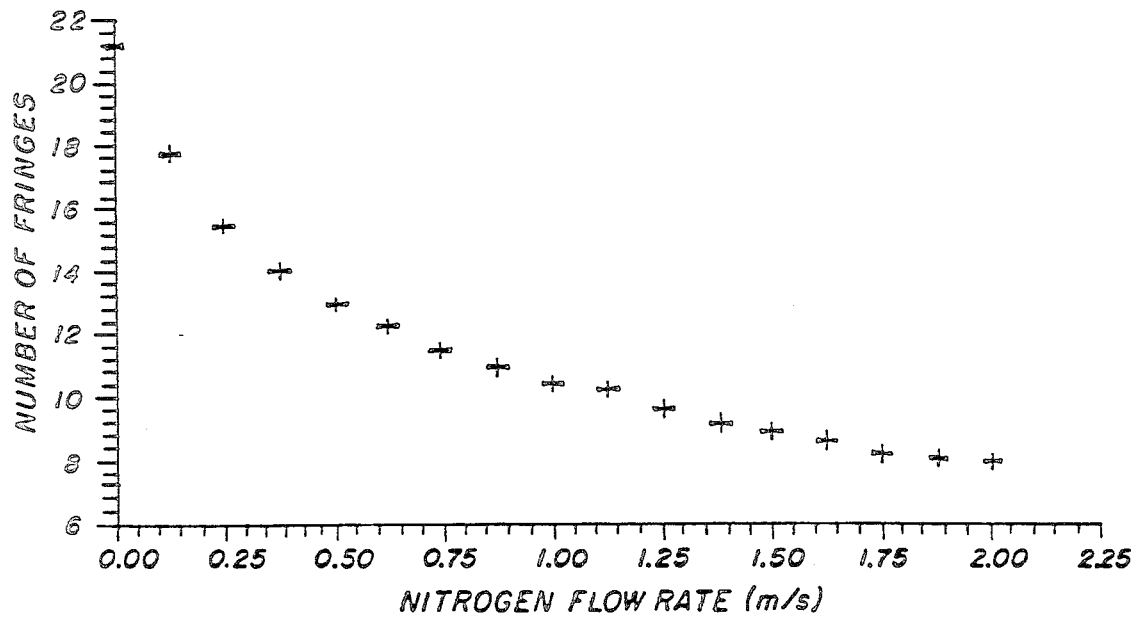
FIG. 8 shows the total number of interference fringes as a function of nitrogen flow rate as measured using the apparatus of FIG. 7.

In FIG. 8 the total number of fringes is plotted as a function of nitrogen flow rate. The flow rates were measured with a conventional hot wire anemometer. This calibration shows very good sensitivity at the lower flow rates allowing very good measurement accuracy. The slope of the curve is less at higher flow rates, but can be increased by increasing the voltage applied to gold coating 14. This suggests an alternative calibration curve: instead of using FIG. 8, one could plot the voltage or power required for 15 or 20 fringes versus the gas flow rate. This type of plot would allow a convenient extension to higher flow rates.

Figure 9:
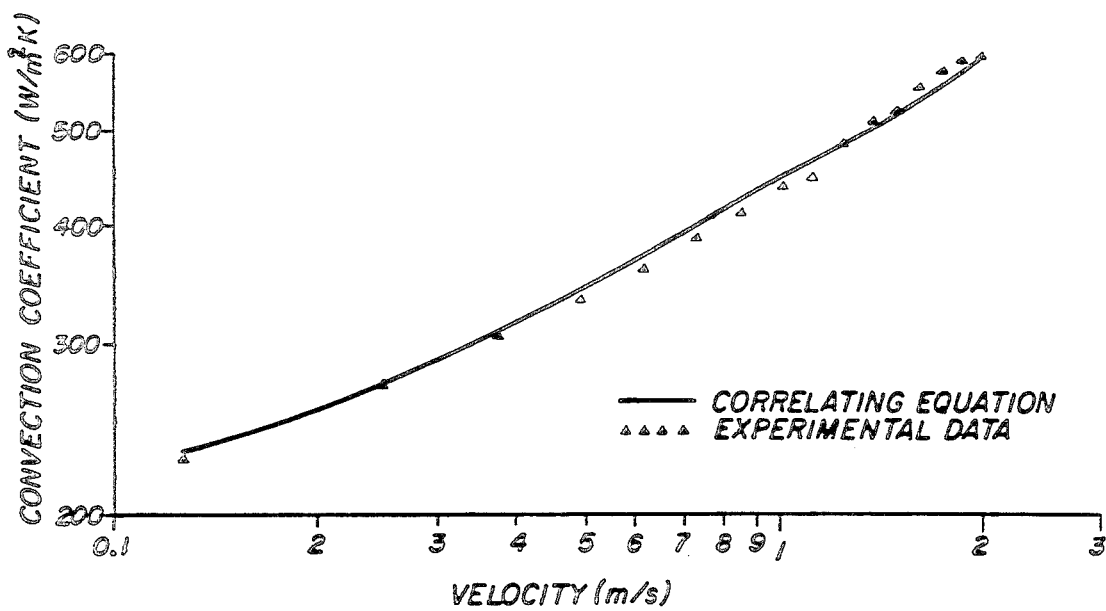
FIG. 9 shows the convective heat flow coefficient for nitrogen gas as a function of flow velocity as determined experimentally using the present invention and theoretically using a correlating equation.

In order to judge the applicability of this method to liquids and to gases other than nitrogen, one could compare the experimental results with results reported in the literature. Churchill and Bernstein have analyzed the voluminous experimental literature concerning heat transfer from a circular cylinder in cross flow and have proposed comprehensive correlating equations ("A Correlating Equation for Forced Convection from Gases and liquids to a Circular Cylinder in Crossflow," Trans. ASME 99, 300 (1977)). For intermediate values of the Reynolds number (Pe>0.2, Re<10,000) they find $$Nu = 0.3 + 0.62RE^{\frac{1}{2}}Pr^{\frac{1}{3}}/[1 + (0.4/Pr)^{\frac{2}{3}}]^{\frac{1}{4}} \qquad (11)$$

where $Nu = 2ah/K_f$, $Re = 2av/v_f$, $Pr = v_f/a_f$, $Pe = RePr$, h is the convection coefficient, $k_f$ is the thermal conductivity of the fluid, v is the velocity of the fluid, $v_f$ is the kinematic viscosity of the fluid, and $a_f$ thermal diffusivity of the fluid. Using this expression, the convection coefficient h was calculated for each of the experimental flow rates. The fluid properties were evaluated at the mean fluid temperature $T_a/2$, where the experimental values of $T_a$ at each flow rate were used. These calculated values were used to plot the solid curve shown in FIG. 9. Experimental values of the forced convection coefficient as a function of nitrogen flow rate were determined using equations (8) and (9) with $P_o = 0.0976$ W, L = 0.01 m, a = 42.6 microns, $k' = 1.3 \times 10^{-8}$ W—m/K and = 0.0027/K. These values of the convection coefficient are also shown in FIG. 9.

The excellent agreement between the experimental values and the published correlation indicate that the device can be used to determine the flow rates of nitrogen at lower and higher flow rates by extrapolation. In addition it appears that the flow rates of other gases and liquids could be determined by using the correlating equation (11) in conjunction with the experimental values of $T_a$. The values of $T_a$ obtained by counting fringes would allow a determination of Nu and Pr. Equation

(11) would then be used to determine Re, and the flow rate v would then be obtained from the value of Re.

The flowmeter device could be modified by introducing a second gold-coated segment of fiber into the flow stream; this segment would be in fiber section 30 of the interferometer and would not be heated, but would respond to temperature and cancel the effects of temperature drift in the sensor arm.

Some of the many advantages of the present invention used to measure the flow rate of fluids should now be readily apparent. In general, the device can measure fluid flows with greater precision than a conventional hot-wire device.

Those skilled in the art will appreciate without any further explanation that many modifications and variations are possible to the above disclosed optical fiber sensor for measuring physical properties of fluids embodiments, within the concept of this invention. Consequently, it should by understood that all such modifications and variations fall within the scope of the following claims.

What we claim is:

1. A method for measuring the flow rate of a fluid using a light transmitting optical fiber, comprising the steps of:
   (a) disposing a conductive material upon the surface of a region of the light transmitting optical fiber;
   (b) disposing at least a portion of said fiber region having said conductive material in the fluid;
   (c) applying light energy to a first end of the light transmitting optical fiber;
   (d) applying electrical energy to said conductive material for a period of time long enough for the fiber to achieve temperature equilibrium;
   (e) receiving transmitted light at a second end of said optical fiber;
   (f) measuring the change in phase of said transmitted light during said period of time; and
   (g) determining the flow rate in accordance with said change in phase and said applied electrical energy.

2. The method of claim 1, wherein the conductive material is gold.

* * * * *